(12) United States Patent
Chuang

(10) Patent No.: US 6,452,500 B1
(45) Date of Patent: Sep. 17, 2002

(54) HYDROCARBON SENSING APPARATUS

(75) Inventor: Hsu-Chen Chuang, Taipei (TW)

(73) Assignee: Hycom Instruments Corp., Taipei (TW)

( * ) Notice: Subject to any disclaimer, the term of this patent is extended or adjusted under 35 U.S.C. 154(b) by 0 days.

(21) Appl. No.: 09/989,473

(22) Filed: Nov. 20, 2001

(30) Foreign Application Priority Data

Nov. 24, 2000 (TW) ..................................... 89220684 U

(51) Int. Cl.[7] .............................................. G08B 21/00
(52) U.S. Cl. ...................... 340/605; 340/620; 73/61.51; 73/61.61; 324/691; 324/697; 324/698; 422/82.02; 436/60; 436/139
(58) Field of Search ................................ 340/605, 620; 422/82.02; 73/61.51, 61.61; 324/697, 698, 691; 436/60, 139

(56) References Cited

U.S. PATENT DOCUMENTS

| | | | | |
|---|---|---|---|---|
| 4,131,773 A | * | 12/1978 | Maham et al. .............. | 324/690 |
| 4,220,041 A | * | 9/1980 | Potter ........................ | 73/61.61 |
| 4,223,552 A | * | 9/1980 | Goldstein ................... | 73/61.61 |
| 4,351,642 A | * | 9/1982 | Bonavent et al. ........... | 340/605 |
| 4,434,650 A | * | 3/1984 | Perry et al. ................ | 73/61.51 |
| 4,549,171 A | * | 10/1985 | Akiba et al. ................ | 340/605 |
| 4,563,674 A | * | 1/1986 | Kobayashi ................... | 340/605 |
| 4,663,614 A | * | 5/1987 | Rauchwerger ............... | 340/605 |
| 5,264,368 A | * | 11/1993 | Clarke et al. ............... | 340/605 |
| 5,444,383 A | * | 8/1995 | Agar et al. ................. | 324/697 |
| 5,514,338 A | * | 5/1996 | Simon et al. ............... | 340/605 |

* cited by examiner

Primary Examiner—Daniel J. Wu
(74) Attorney, Agent, or Firm—Connolly Bove Lodge & Hutz

(57) ABSTRACT

An apparatus for monitoring presence of hydrocarbon-based fluid is disclosed. It includes a body and a sensing cable mounted on the body in a wave-like shape, thus forming a plurality of sensing sections for detecting a layer of hydrocarbon on water. When contacting hydrocarbon, each of the sensing sections generates a signal and the signals add up before transmission to a signal receiver through a signal line.

8 Claims, 5 Drawing Sheets

HYDROCARBON SENSING APPARATUS

BACKGROUND OF INVENTION

1. Field of Invention

The present invention relates to a hydrocarbon-sensing apparatus and, more particularly, to a conductive polymer-based hydrocarbon-sensing apparatus including multiple sensing sections for contacting a layer hydrocarbon.

2. Description of Related Art

Pollution of reservoirs, rivers, or groundwater has new become a global problem. Such pollution may be caused by illegally dumping waste into water source. Moreover, oil may leak from tanks or pipes broken in an earthquake, for example. Thus, severe contamination of environment occurs.

Hydrocarbon-based fluid such as gasoline or diesel has a specific gravity smaller than that of water. Therefore, hydrocarbon-based fluid tends to float on water. When tanks that contain hydrocarbon-based fluid are located on the ground for some time, the hydrocarbon-based fluid is very likely to leak from the tanks. Hydrocarbon-based fluid that leaks from a tank may penetrate the ground so as to float on groundwater. Various devices have been devised for detecting contamination of groundwater caused by hydrocarbon fluid. Such devices can be found in U.S. Pat. Nos. 4,131,773, 4,223,552, 4,434,650, 4,563,674, 5,264,368, 5,444,383 and 5,514,338.

FIG. 1 shows a conventional hydrocarbon leak sensor incorporating a probe P. A portion of probe P is immersed in a well to be monitored and an upper end of probe P is fixed onto the wall of the well. Probe P incorporates a petroleum sensor made of conductive polymer in the form of a cable, for example, AMC-5016 (1932TC) made and sold by a Canada-based company, Armstrong Monitoring Corporation. The resistivity of such petroleum sensor is about several KΩ/m in the air or water and rises dramatically to about 20MΩ/m when such petroleum sensor contacts hydrocarbon or petroleum. Rise in resistivity of such petroleum sensor can be taken as presence of hydrocarbon or petroleum. The resistance (the unit is Ω) of probe P rises at a lower rate and to a smaller extent as a shorter section of probe P contacts hydrocarbon. In practice, probe P can be used to detect presence of a layer of hydrocarbon as thin as 0.8 mm. The rise of the resistance of probe P is too small to recognize when probe P contacts a layer of hydrocarbon thinner than 0.8 mm. Therefore, probe P cannot sense hydrocarbon leak or spill at an early stage. Furthermore, when leaking or spilling at a low flow rate, due to vaporization, hydrocarbon may not form a layer thick enough for probe P to sense. In other words, it is unlikely to be able to detect a leak or spill before significant damage has occurred. Moreover, a hydrocarbon layer on groundwater cannot be sensed when the groundwater surface rises above the upper end of probe P or when the groundwater surface descends below a lower end of probe P. To overcome this drawback, a lengthened probe is required. However, this increases cost and limits its applications.

Thus, it is desirable to provide an improved hydrocarbon sensor in order to overcome the above-mentioned drawbacks encountered in prior art.

SUMMARY OF INVENTION

It is an objective of the present invention to provide an apparatus for monitoring presence of hydrocarbon-based fluid wherein a sensing cable is provided in a wave-like arrangement. Thus, the sensing cable includes a number of sensing sections for contacting a layer of hydrocarbon-based fluid on the water surface. When contacting a layer of hydrocarbon-based fluid, the sensing sections generate a corresponding number of signals that add up to increase the signal intensity. A layer of hydrocarbon-based fluid can thus be sensed by means of the sensing cable even it is very thin. That is, the present invention can warn of hydrocarbon leak at an early stage or at a low flow rate so that an appropriate action can be taken before significant damage is made.

It is another objective of the present invention to provide an apparatus for monitoring presence of hydrocarbon-based fluid wherein a sensing cable is provided on a buoy for floating on the water surface. Thus, it is assured that the sensing cable always contact a layer of hydrocarbon-based fluid on the water surface no matter how the water surface changes.

To accomplish the above objects and features, the apparatus of the present invention comprises a buoy for floating on the water surface and a sensing cable made of conductive polymer. The sensing cable is mounted on a periphery of the buoy in a wavelike shape, thus forming a plurality of sensing sections for contacting a layer of hydrocarbon-based fluid on the water surface. When contacting a layer of hydrocarbon-based fluid, a signal is generated in. each of the sensing sections, and the signals add up before transmitting to the monitoring and warning unit through the signal line. By utilizing this, a sensitivity of a hydrocarbon-sensing apparatus is significantly increased according to the present invention.

The above and other objects, features and advantages of the present invention will become apparent from the following description taken with the attached drawings.

DETAILED DESCRIPTION OF PREFERRED EMBODIMENT

Figure 1:
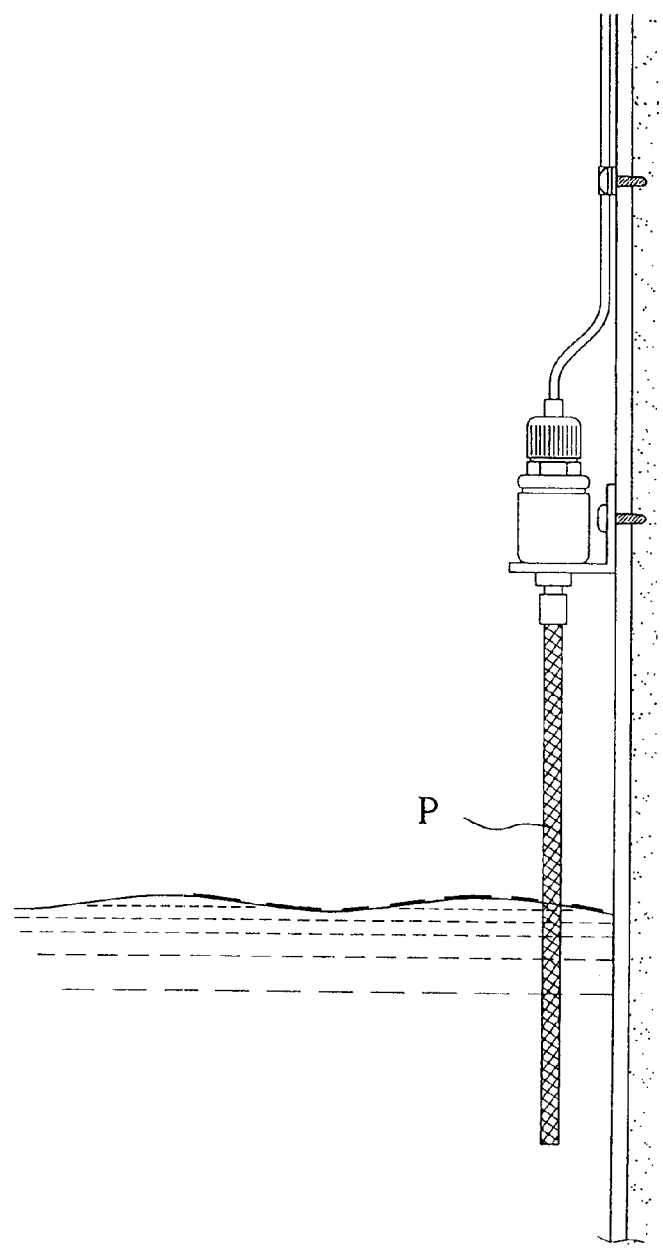
FIG. 1 is a side view of a conventional hydrocarbon-sensing device.
Figure 2:
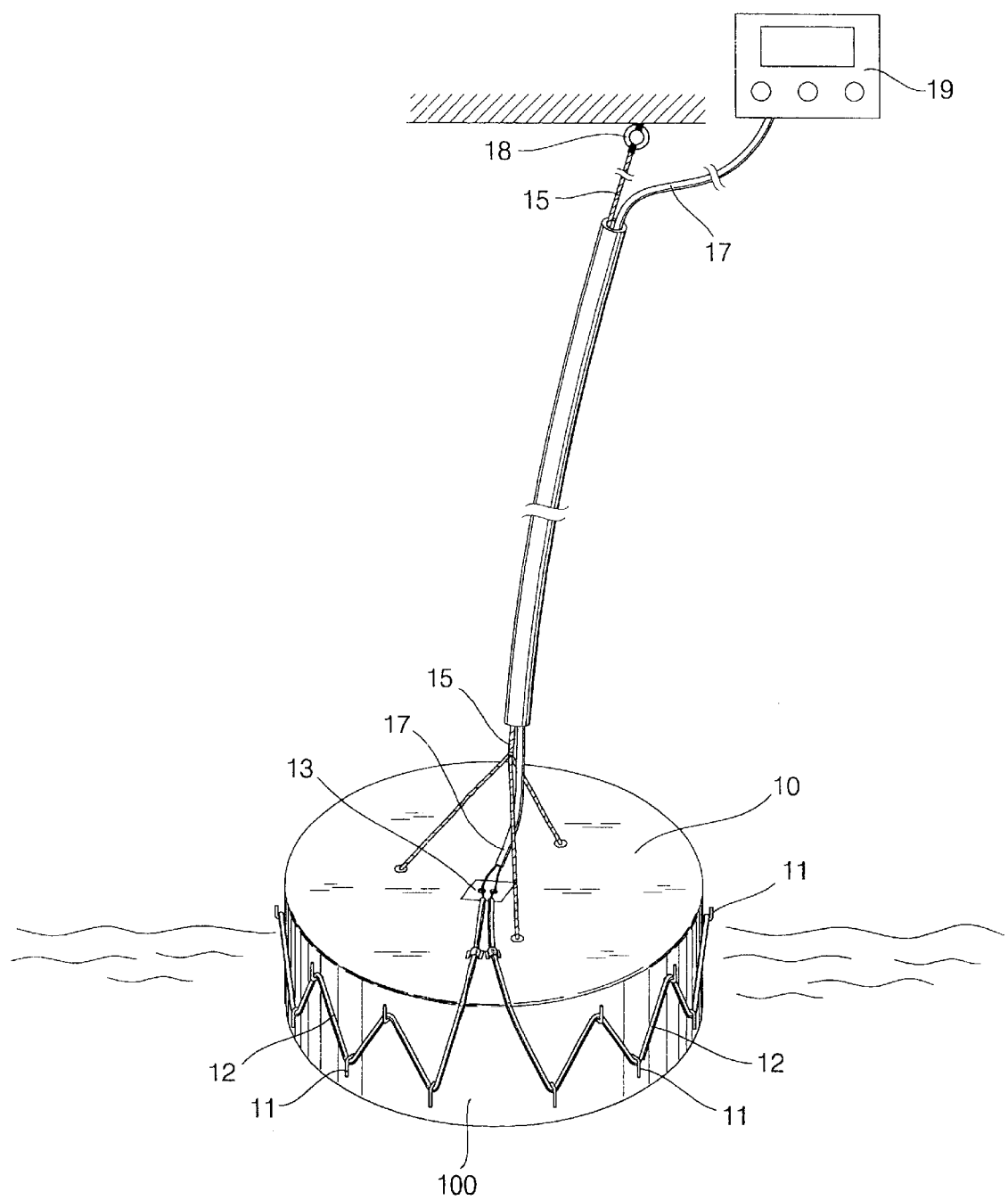
FIG. 2 is a perspective view of a first embodiment of the hydrocarbon-sensing apparatus according to the present invention.
Figure 3:
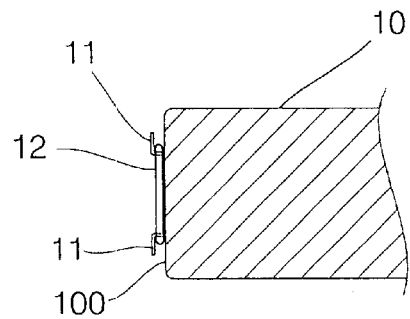
FIG. 3 is a cross-sectional view of a buoy and a sensing cable of FIG. 2.

FIGS. 2 to 5 show a first embodiment of a hydrocarbon-sensing apparatus made in accordance with the present invention. The apparatus includes an essential component, sensing cable 12. In the preferred embodiments, sensing cable 12 is AMC-5016 (1932TC) manufactured and sold by a Canada-based company, Armstrong Monitoring Corporation, and therefore is not described in detail for brevity. The resistivity of sensing cable 12 is about several KΩ/m in the air or water and rises dramatically to about 20MΩ/m when sensing cable 12 contacts hydrocarbon. The resistance (its unit is Ω) of sensing cable 12 rises at a lower rate and to a smaller extent as a shorter section of sensing cable 12 contacts hydrocarbon. In practice, sensing cable 12 can be used to detect presence of a layer of hydrocarbon as thin as 0.8 mm if it includes only one section in contact with the layer of hydrocarbon. When a layer of hydrocarbon gets thinner than 0.8 mm, the rise of the resistance of sensing cable 12 is too small to recognize. To achieve a highly sensitive hydrocarbon-sensing apparatus, sensing cable 12 is arranged in a novel manner in accordance with the present invention to be described in detail.

The apparatus of the present invention includes a drum-like buoy 10 for floating on the water surface. A number of hooks 11 are provided on the periphery 100 of buoy 10 in order to hook sensing cable 12, thus securing sensing cable 12 to buoy 10 and making sensing cable 12 in a wavelike shape. On a top of buoy 10, two ends of sensing cable 12 are connected with a contact terminal 13. A signal line 17 is connected between contact terminal 13 and a remote monitoring and warning unit 19.

Figure 4:
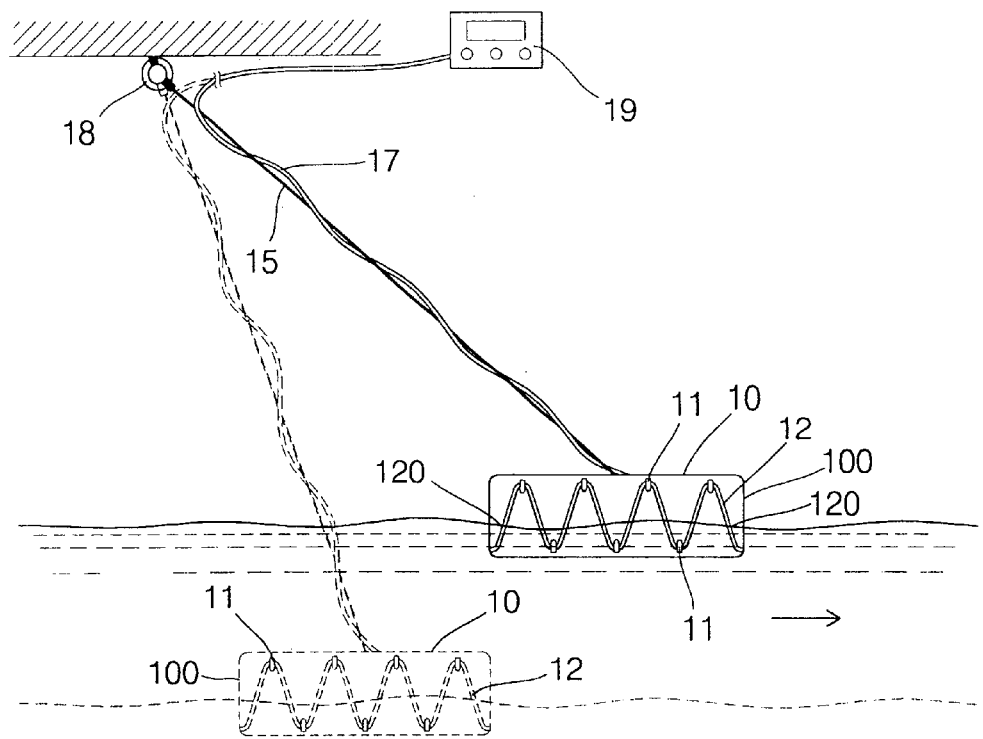
FIG. 4 is a side view showing the buoy and a portion of the sensing cable in different positions as the water surface changes.

It is clearly shown in FIG. 4 that a number of sensing sections 120 of sensing cable 12 can contact a layer of hydrocarbon on the water surface due to the wavelike shape of the sensing cable 12 mounted on periphery 100 of buoy 10. Thus, when contacting hydrocarbon, each sensing section 120 produces a signal representative of the rise of the resistance. The signals respectively generated in sensing sections 120 add up so as to increase a total intensity (i.e., amplified), thus significantly increasing sensitivity of hydrocarbon sensing. Accordingly, even a layer of hydrocarbon (or petroleum) is less than 0.8 mm thick (0.1 mm in practice), the increase of the resistance of the entire length of sensing cable 12 is still obvious in accordance with the present invention. Such multiple sensing section arrangement of the present invention can alert about leak or spill at an early stage or at a low flow rate promptly by monitoring and warning unit 19 detecting a significant change of the resistance of sensing cable 12. Therefore, appropriate actions can be taken before significant damages occur.

When used in open water, the apparatus of the present invention is vulnerable to strong wind and water flow. The signal line 17 would be easily torn. To resist such strong wind and water flow, a steel cable 15 is used. Steel cable 15 is connected between the top of buoy 10 and a ring 18 attached to the ground. In addition, steel cable 15 is bound with a section of signal line 17. Thus, possible forces exerted by strong wind and water flow are taken by steel cable 15 instead of signal line 17.

Figure 5:
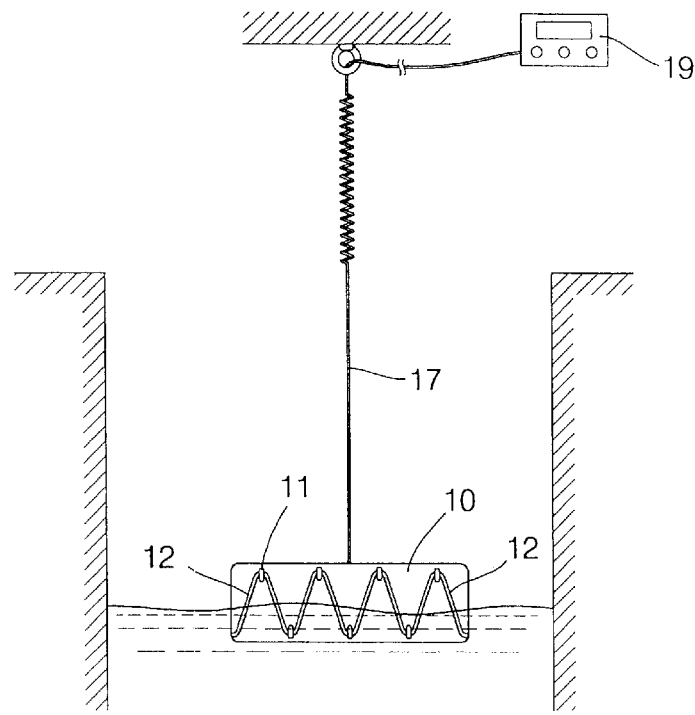
FIG. 5 is a perspective view showing another configuration of the hydrocarbon-sensing apparatus wherein a signal line includes a helical section for fluctuating on the water surface in a monitoring well.

When used in still water such as in a well where a float goes up and down together with the water surface but does not drift due to no strong wind or water flow, steel cable 15 is not necessary. FIG. 5 shows another configuration without use of steel cable 15. In this configuration, signal line 17 includes a helical section for providing elasticity in a vertical direction for adjusting a vertical distance between upper and lower ends of signal line 17 to a smallest possible value.

It is further noted that the provision of monitoring and warning unit 19 is optional. In an alternative configuration, monitoring and warning unit 19 is replaced with a signal receiver (not shown) provided on the ground near the location of fluid to be monitored. The signal receiver unit may be further connected to monitoring and warning unit 19.

Moreover, signal received from sensing cable 12 is sent to a remote monitoring station via the signal receiver unit through wireless means or fiber-optic (not shown).

Figure 6:
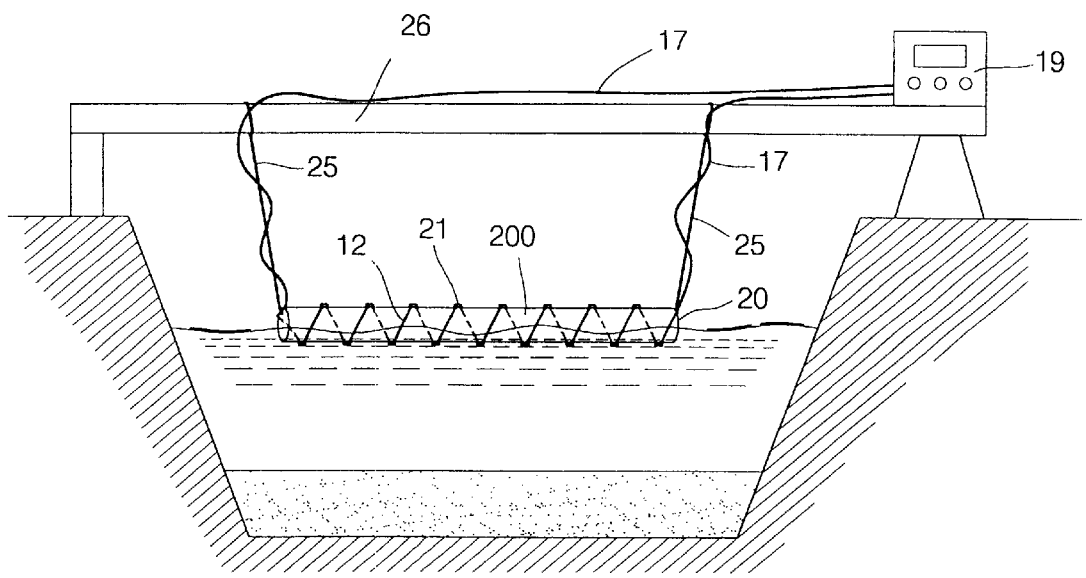
FIG. 6 is a side view of a second embodiment of the hydrocarbon-sensing apparatus according to the invention.
Figure 7:
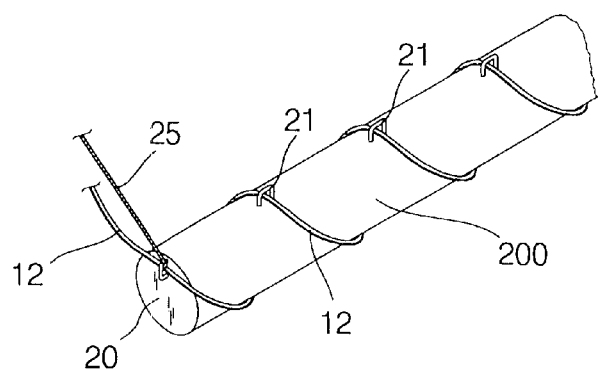
FIG. 7 is a perspective view of a buoy and a sensing cable of FIG. 6.
Figure 8:
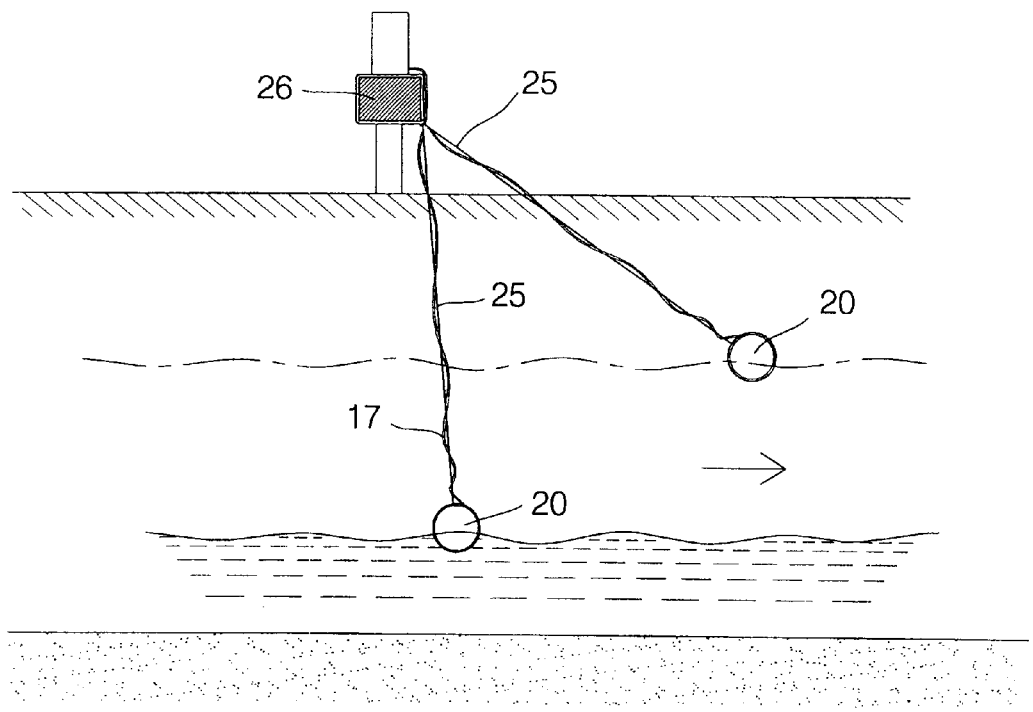
FIG. 8 is a side view showing the buoy and a portion of the sensing cable in different positions as the water surface varies.

FIGS. 6 to 8 show a second embodiment of the hydrocarbon-sensing apparatus constructed in accordance with the invention. The differences between second and first embodiments are detailed below. Buoy 20 is an elongate hollow cylinder or bar. A bracket 26 is provided across a river or other waterway. Two steel cables 25 each have one end secured to bracket 26 and another end secured to one end of buoy 20. A sensing cable 12 is helically wrapped around buoy 20. A plurality of spaced hooks 21 are provided on a periphery of buoy 20 for hooking a corresponding number of sections of sensing cable 12, thus securing sensing cable 12 to buoy 20. Two ends of signal line 17 are coupled to two ends of sensing cable 12 directly and then connected to a monitoring and warning unit 19 or a signal receiver unit (not shown). This embodiment has the same effect as the first embodiment mentioned above and the same components or portions as the first one embodiment are given the same reference numbers for easy reference thus the related descriptions are omitted.

It is noted that alternatively, for forming a wavelike shape of sensing cable 12 on the periphery (100, 200) of the buoy (10, 20), a continuous wavelike recess (not shown) may be defined in the periphery (100, 200) of the buoy (10, 20) for mounting the sensing cable (12) thereon. Therefore, hooks 11 or 21 are not necessary elements in accordance with the present invention and can be omitted in other embodiments.

While the invention herein disclosed has been described by means of specific embodiments, numerous modifications and variations could be made thereto by those skilled in the art without departing from the scope and spirit of the invention set forth in the claims.

What is claimed is:

1. An apparatus for monitoring presence of hydrocarbon-based fluid comprising a body and a sensing cable mounted on the body in a wave-like shape, thus forming a plurality of sensing sections for detecting a layer of hydrocarbon on water; wherein when contacting hydrocarbon, each of the sensing sections generates a signal and the signals add up before transmission to a signal receiver through a signal line.

2. The apparatus of claim 1, wherein the sensing cable is formed of conductive polymer including a first resistance in the air or water and a second resistance larger than the first resistance when contacting hydrocarbon.

3. The apparatus of claim 1, wherein the body is a buoy for floating on water.

4. The apparatus of claim 3, wherein the buoy is shaped like a drum.

5. The apparatus of claim 3, further comprising a steel cable connected between the buoy and a proper stationary position with respect to the ground.

6. The apparatus of claim 3, wherein the buoy is shaped like a cylinder.

7. The apparatus of claim 6, wherein the sensing cable is helically wrapped around the buoy.

8. The apparatus of claim 1, further comprising a plurality of hooks mounted on a periphery of the buoy for engagement with various portions of the sensing cable, thus forming the wavelike shape of the sensing cable.

* * * * *